United States Patent
Browne et al.

(10) Patent No.: US 9,408,968 B2
(45) Date of Patent: Aug. 9, 2016

(54) METHOD AND APPARATUS FOR DETECTION AND MANAGEMENT OF AIR-IN-LINE

(75) Inventors: Aidan Browne, Murrieta, CA (US); Jeffery T. Juretich, Herriman, UT (US); Ramji Gupta, Williamsville, NY (US); Daniel A. Martel, Stansbury Park, UT (US)

(73) Assignee: Zevex, Inc., Salt Lake City, UT (US)

( * ) Notice: Subject to any disclaimer, the term of this patent is extended or adjusted under 35 U.S.C. 154(b) by 1082 days.

(21) Appl. No.: 13/531,554

(22) Filed: Jun. 24, 2012

(65) Prior Publication Data

US 2013/0345658 A1    Dec. 26, 2013

(51) Int. Cl.
    *A61M 5/168*    (2006.01)
    *A61M 5/142*    (2006.01)
    *A61M 5/36*     (2006.01)

(52) U.S. Cl.
    CPC ....... *A61M 5/16831* (2013.01); *A61M 5/14232* (2013.01); *A61M 5/36* (2013.01); *A61M 5/365* (2013.01); *A61M 2005/14208* (2013.01); *A61M 2005/16868* (2013.01); *A61M 2005/16872* (2013.01)

(58) Field of Classification Search
    CPC ............... A61M 5/16831; A61M 5/14232; A61M 5/36; A61M 5/365; A61M 2005/14208; A61M 2005/16868; A61M 2005/16872
    See application file for complete search history.

(56) References Cited

U.S. PATENT DOCUMENTS

| | | | |
|---|---|---|---|
| 5,000,663 A | 3/1991 | Gorton | |
| 5,616,124 A * | 4/1997 | Hague | A61M 5/365 128/DIG. 13 |
| 6,531,708 B1 | 3/2003 | Malmstrom et al. | |
| 6,616,633 B1 | 9/2003 | Butterfield et al. | |
| 6,750,468 B2 | 6/2004 | Malmstrom et al. | |
| 7,141,037 B2 | 11/2006 | Butterfield et al. | |
| 7,726,174 B2 | 6/2010 | Riley et al. | |
| 7,805,978 B2 | 10/2010 | Riley et al. | |
| 7,818,992 B2 | 10/2010 | Riley et al. | |
| 7,987,722 B2 | 8/2011 | Hills | |

(Continued)

FOREIGN PATENT DOCUMENTS

| | | |
|---|---|---|
| CA | 2670512 A1 | 7/2008 |
| EP | 0293592 | 12/1988 |

(Continued)

OTHER PUBLICATIONS

WIPO—ISA/US—International Search Report mailed Oct. 9, 2013 in corresponding International Application No. PCT/US2013/046594.

(Continued)

*Primary Examiner* — Emily Schmidt
*Assistant Examiner* — Lauren M Peng
(74) *Attorney, Agent, or Firm* — Hodgson Russ LLP (57) ABSTRACT

In an infusion pump operable to deliver fluid to a patient at a programmed therapy flow rate, air-in-line sensing is improved by commanding the pumping mechanism to deliver a bolus volume of fluid at a flow rate higher than the therapy flow rate when an uninterrupted volume of air is detected that exceeds a first threshold. In many cases, the bolus will be effective to clear microbubbles from an observation zone of the air-in-line sensor to avoid an air-in-line alarm condition. If the uninterrupted volume of air continues to grow beyond a second threshold in spite of the bolus, then an alarm may be triggered. The invention reduces false alarms.

16 Claims, 8 Drawing Sheets

(56) References Cited

U.S. PATENT DOCUMENTS

| 2008/0103445 | A1 | 5/2008 | Blaine et al. |
| 2009/0053071 | A1 | 2/2009 | Wang et al. |
| 2010/0212407 | A1 | 8/2010 | Stringham et al. |
| 2010/0306986 | A1 | 12/2010 | Riley et al. |
| 2011/0036143 | A1 | 2/2011 | Riley et al. |
| 2012/0035535 | A1 | 2/2012 | Johnson et al. |

FOREIGN PATENT DOCUMENTS

| GB | 2312046 | 10/1997 |
| JP | 2011177411 | 9/2011 |
| JP | 2012072991 | 4/2012 |

OTHER PUBLICATIONS

WIPO—ISA/US—Written Opinion of the International Searching Authority mailed Oct. 9, 2013 in corresponding International Application No. PCT/US2013/046594.

Zevex, Inc.—Informal Comments Regarding Written Opinion of International Search Authority filed Nov. 14, 2014 with the International Bureau in corresponding International Application No. PCT/US2013/046594.

* cited by examiner

Fig. 4
*MICROBUBBLE DETECTION*

Fig. 5
*BOLUS COMPENSATION*

METHOD AND APPARATUS FOR DETECTION AND MANAGEMENT OF AIR-IN-LINE

FIELD OF THE INVENTION

The present invention relates to the field of medical infusion pumps, and more particularly to air-in-line sensing and management methods for medical infusion pumps.

BACKGROUND OF THE INVENTION

Programmable infusion pumps for delivering nutritional liquids and medicine to patients in accordance with predetermined liquid delivery parameters are in wide usage. One type of infusion pump is a peristaltic pump arranged along flexible connective tubing carrying liquid from a liquid source to the patient. The peristaltic pump has a pumping mechanism for progressively squeezing successive portions of the tubing to cause fluid to flow through the tubing in a flow direction toward the patient. In a common arrangement, the pumping mechanism includes a motor-driven wheel having radial fingers or rollers that engage a segment of the tubing arranged about a circumferential portion of the wheel. As the wheel rotates, fluid is pumped through the tubing to the patient. The tubing segment arranged about the pump wheel may be held in a U-shaped configuration by a cassette designed for receipt in a channel or receptacle area of the pump. The cassette may provide terminals for connecting an incoming line of tubing coming from the liquid source and an outgoing line of tubing going to the patient to opposite ends of the U-shaped tubing segment received by the pump.

A recognized safety concern when pumping nutritional liquids for enteral feeding or medicinal fluids for intravenous therapy is the formation of air bubbles in the liquid being pumped into the patient. As a safety measure, it is known to provide an air-in-line sensor on the infusion pump for detecting an air-in-line condition and triggering an alarm. For example, the air-in-line sensor may include an ultrasonic transmitter arranged to direct ultrasound through the tubing and a receiver on an opposite side of the tubing from the transmitter for receiving the ultrasound waves after passage through the tubing and the fluid carried thereby. The receiver generates an output signal indicating whether the ultrasound signal passed through liquid or air as it travelled from the transmitter to the receiver.

The air-in-line sensor output is sampled regularly as fluid is pumped through the tubing to observe each incremental volume of fluid passing through the sensor's zone of observation. In known air bubble detection algorithms, an air-in-line alarm condition is detected when a series of consecutive sensor readings indicate that a predetermined volume of air has passed the sensor (e.g. 1.5 milliliters) without the presence of a predetermined volume of liquid (e.g. 0.375 milliliters).

A problem has been identified that occurs when food bottles containing a nutritional liquid are vigorously shaken to mix the contents. In such cases, micro-bubbles may collect at the downstream side of the air-in-line sensor and may eventually cause an air-in-line alarm. The delivery of fluid by the pump may be implemented in discrete time segments during which the pump's motor is actually on and pumping only a small portion of the time segment, and is off for the remainder of the time segment. Due to gravity, air microbubbles caused by shaking may float upstream and gather at the air-in-line sensor, potentially causing detection of an air-in-line condition which will trigger a "false" alarm.

A need exists to prevent this type of false alarm, preferably without changing the pump hardware or sensor hardware.

SUMMARY OF THE INVENTION

The present invention addresses the problem mentioned above, and does so without changes to the pump hardware or sensor hardware, which are optimized for other key considerations.

In one aspect, the invention provides a method of detecting an air-in-line condition with respect to flow of liquid through tubing connected to an infusion pump. The method generally comprises the steps of (i) providing an air-in-line sensor at a sensing location along the tubing, the air-in-line sensor generating a signal indicating whether a volume of fluid observed by the sensor at a given time is air or liquid; (ii) operating the pump to deliver fluid at a therapy flow rate; (iii) sampling the sensor signal as fluid flows past the sensor; (iv) calculating a total volume of air observed by the sensor since the sensor last observed liquid; (v) operating the pump to deliver a bolus volume of fluid at a bolus flow rate greater than the therapy flow rate when the total volume of air exceeds a first threshold; and (vi) detecting the air-in-line condition when the total volume of air exceeds a second threshold greater than the first threshold. In the method above, the bolus delivery in step (v) is often effective to clear accumulated air bubbles to avoid an air-in-line condition requiring an alarm.

The method summarized above may further comprise the step of operating the pump to deliver fluid at a reduced flow rate less than the therapy flow rate after delivery of the bolus volume in order to compensate for excess volume delivered via the bolus volume. The pump may be operated at the reduced flow rate until the excess volume delivered relative to the therapy flow rate as a result of the delivery of the bolus volume is compensated for, and then at the therapy flow rate to resume the programmed therapy.

In another aspect, the present invention provides a method of clearing air microbubbles from an observation zone of an air-in-line sensor arranged to observe fluid flowing through tubing connected to an infusion pump. The method generally comprises the steps of (i) calculating a total volume of air observed by the sensor since the sensor last observed liquid; and (ii) operating the pump to deliver a bolus volume of fluid at a bolus flow rate greater than a programmed therapy flow rate when the total volume of air exceeds a predetermined threshold. The bolus flow rate may be substantially equal to a priming flow rate used for priming the pump.

In another aspect, the invention encompasses an infusion pump generally comprising (i) a pumping mechanism operable to cause fluid flow through tubing connected to the pumping mechanism, the pumping mechanism including a motor and a motor controller for energizing the motor; (ii) an air-in-line sensor arranged at a sensing location along the tubing to observe fluid flowing through the tubing, the air-in-line sensor generating a signal indicating whether a volume of fluid observed by the sensor at a given time is air or liquid; (iii) a memory module; and (iv) a microprocessor connected to the memory module, the pumping mechanism and the air-in-line sensor, wherein the microprocessor is programmable to command the pumping mechanism deliver fluid at a therapy flow rate, wherein the memory module stores programming instructions causing the microprocessor to command the pumping mechanism to deliver a bolus volume of fluid at a bolus flow rate greater than the therapy flow rate in response to signals from the air-in-line sensor indicating an uninterrupted volume of air flowing through the tubing is greater than a predetermined first volume threshold.

The memory module may also store programming instructions causing the microprocessor to register an air-in-line alarm condition in response to signals from the air-in-line sensor indicating an uninterrupted volume of air flowing through the tubing is greater than a predetermined second volume threshold greater than the first volume threshold.

To compensate for excess volume delivered by the bolus, the memory module may store programming instructions causing the microprocessor to command the pumping mechanism to deliver fluid at a reduced flow rate less than the therapy flow rate after delivery of the bolus volume. The reduced flow rate may be a predetermined percentage of the therapy flow rate, for example 50%. The memory module may also store further programming instructions causing the microprocessor to command the pumping mechanism to deliver fluid at the therapy flow rate after excess volume compensation is complete.

BRIEF DESCRIPTION OF THE DRAWING VIEWS

The invention is described in detail below with reference to the following figures.

DETAILED DESCRIPTION OF THE INVENTION

Figure 1:
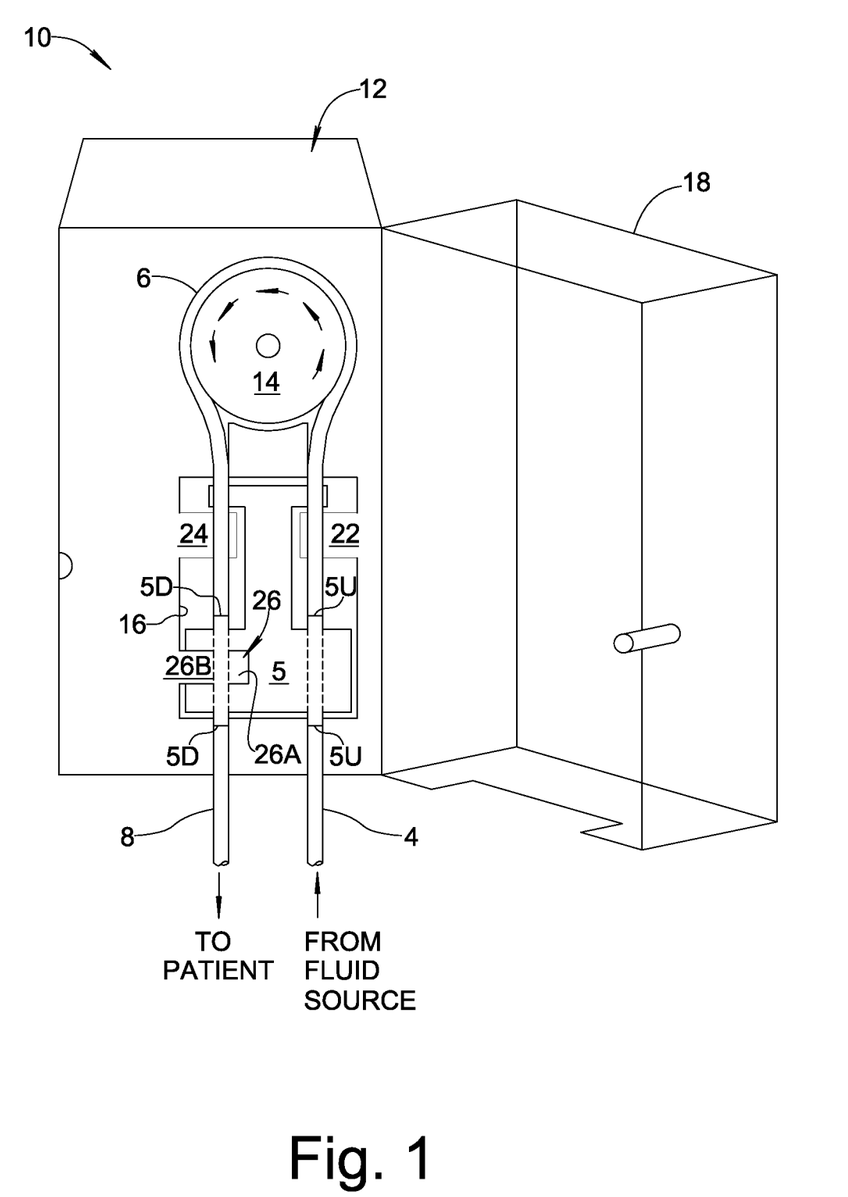
FIG. 1 is schematic representation of an infusion pump formed in accordance with an embodiment of the present invention, wherein a cassette and tubing are shown installed in the pump to illustrate basic operation.
Figure 2:
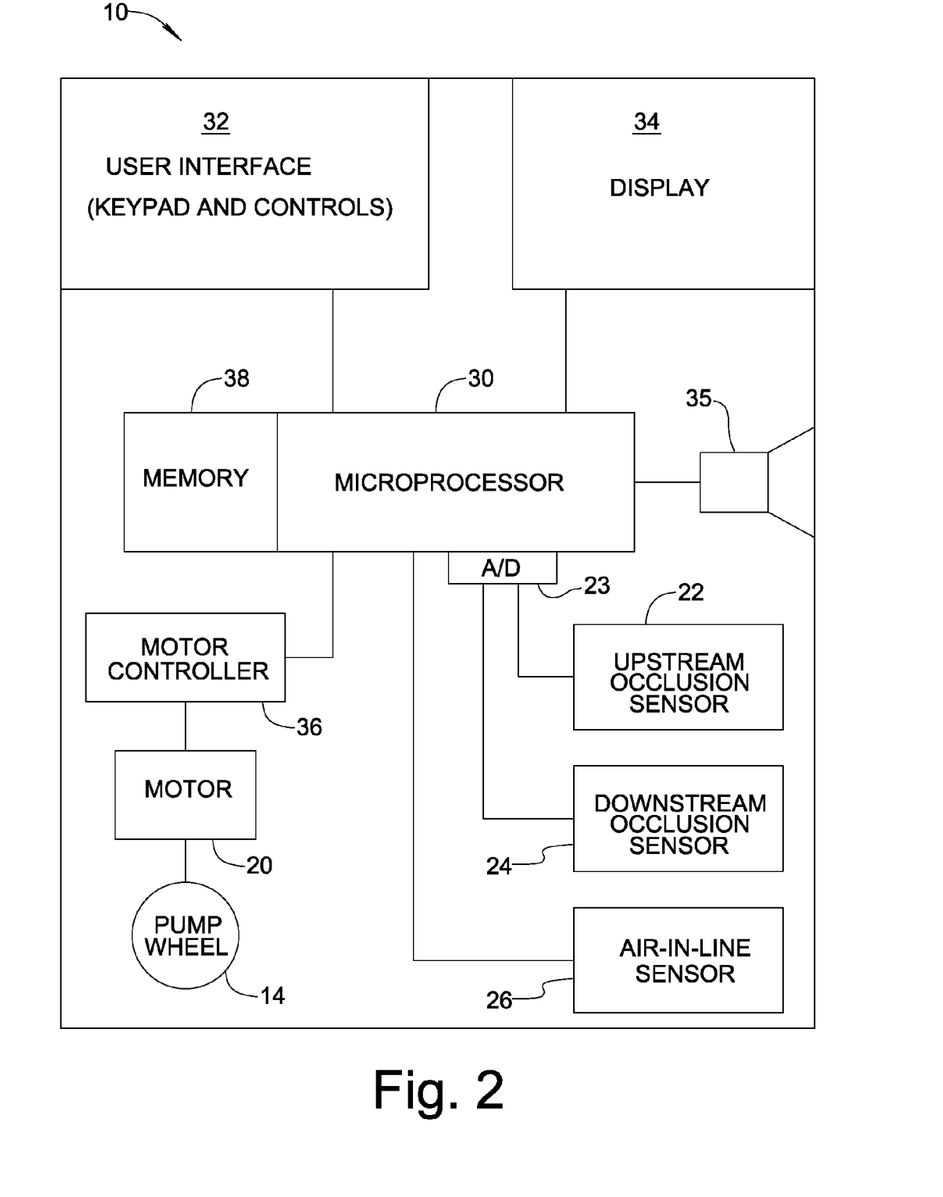
FIG. 2 is an electronic block diagram of the infusion pump shown in FIG. 1.

FIGS. 1 and 2 schematically depict a programmable infusion pump 10 embodying the present invention. Infusion pump 10 includes a housing 12, a pump wheel or rotor 14 and a cassette receptacle 16 on an external face of the housing, and a door 18 connected to the housing to open and close over the cassette receptacle and pump wheel. As shown in FIG. 1, an administration set may be installed in association with the pump for carrying fluid from a fluid source to a patient. The administration set may include upstream tubing 4 running from the fluid source to the pump, downstream tubing 8 running from the pump to a patient, a cassette 5 received in cassette receptacle 16, and a U-shaped tubing segment 6 arranged around pump wheel 14. Cassette 5 is configured with connection terminals 5U and 5D for connecting upstream tubing 4 to an upstream end of tubing segment 6 and downstream tubing 8 to a downstream end of tubing segment 6 to complete a flow path from the upstream tubing to the downstream tubing via the pump.

Pump wheel 14 is part of a pumping mechanism operable to cause fluid flow through the tubing in an intended flow direction. The pumping mechanism further includes an electric motor 20 connected to pump wheel 14 and operable to rotate the pump wheel about its axis. Pump wheel 14 has radial fingers or rollers (not shown) that engage tubing segment 6 arranged about a circumferential portion of the wheel. When pump wheel 14 rotates, successive portions of tubing segment 6 are progressively squeezed to cause fluid to flow through the tubing in a flow direction toward the patient. The flow rate of infused fluid may be controlled by controlling the rate at which motor 20 is driven and/or the length of time motor 20 is driven at a given rate. Those skilled in the art will understand that variations of the peristaltic pumping mechanism described above are possible. For example, motor 20 may drive a cam member connected to a series of parallel fingers or rollers arranged side-by-side, whereby peristaltic pumping action is applied to a straight segment of tubing instead of a curved segment of tubing as shown in FIG. 1. The present invention is not limited to a specific pumping mechanism configuration.

Infusion pump 10 may be provided with an upstream occlusion sensor 22 at a location along tubing segment 6 upstream from pumping wheel 14 and a downstream occlusion sensor 24 at a location along tubing segment 6 downstream from pumping wheel 14. Upstream sensor 22 and downstream sensor 24 each provide a respective sensor signal indicative of a respective local fluid pressure in the tubing. For example, upstream and downstream sensors 22, 24 may be transducers or strain gauges arranged to engage an outer wall of tubing segment 6 to detect deflection of the flexible tubing wall caused by fluid pressure within the tubing and provide an electronic signal proportional to the deflection.

Infusion pump 10 further includes an air-in-line sensor 26 for detecting whether a volume of fluid observed by the sensor at a given time is air or liquid. In the present embodiment, air-in-line sensor 26 may comprise an ultrasonic transducer which includes a pair of piezoelectric ceramic elements 26A and 26B opposing each other across a portion of tubing segment 6. One ceramic element 26A is driven by microprocessor 30 at a frequency that sweeps through the resonance which lies within the frequency range. The ultrasonic energy is transmitted by element 26A into one side of the tubing and a portion of the energy is received by element 26B on the other side. If liquid is present in the tubing, the ultrasonic energy received by element 26B will be greater than a preset comparator threshold and is then converted into a logic level of "High". If air is present in the tubing, the medium for propagating the ultrasonic energy is less dense and the signal generated by element 26B is attenuated below the threshold and is converted into a logic level of "Low". Thus, in the embodiment just described, the amplitude of the ultrasonic energy which is received by element 26B is the main principle for determining the difference between liquid and air within the tubing. The tubing may be dry-coupled to the air-in-line sensor elements 26A and 26B; i.e. the sensor arrangement does not require the use of ultrasonic gel.

As seen in FIG. 2, infusion pump 10 is configured to permit a user to select and/or create, and then run, an infusion therapy protocol determining the amount of liquid to be delivered to the patient and the rate at which the liquid is to be delivered.

Infusion pump 10 includes a microprocessor 30 connected to a user interface 32 having input devices such as a keypad, switches and dial controls. Infusion pump 10 also includes a display 34 connected to microprocessor 30. Display 34 may be a touch screen display acting at times as part of user interface 32. Microprocessor 30 is connected to a motor controller 36 for driving electric motor 20 to administer a chosen therapy protocol. One or more memory modules 38 are connected to or integrated with microprocessor 30 for storing instructions executable by the microprocessor for controlling pump operation. The stored instructions may be organized in software routines. Among the stored software routines are routines that detect possible microbubbles, attempt their removal through release of a bolus, and compensate for excess fluid delivered by the bolus to achieve the programmed therapy delivery rate. These routines are described in detail below. For purposes of the present invention, microprocessor 30 receives the signal from air-in-line sensor 26. Microprocessor 30 is also connected to upstream occlusion sensor 22 and downstream occlusion sensor 24. Analog-to-digital conversion circuitry 23 is shown for converting the analog voltage signals from the occlusions sensors to digital form for use by microprocessor 30, however other forms of occlusion sensor and microprocessor interfaces may be used. Infusion pump 10 may also include an audible signal generator 35 connected to microprocessor 30.

In an embodiment of the present invention, fluid delivery is implemented in regular time segments, for example one-minute segments. A therapy flow rate may be selected within a range of 0.1 milliliters per hour (ml/hr) to 400 ml/hr. Motor 20 may be operated at a given rotational speed, for example 40 rpm. By way of example, each motor rotation may include 12 incremental rotational motor steps or "ticks", wherein the resolution of fluid delivery is 18 microliters per tick. Thus, approximately 56 ticks are required to pump 1 milliliter of fluid. If the selected therapy rate is 60 ml/hr, then an average of 1 milliliter must be pumped during each one-minute segment. Assuming the motor is operating at 40 rpm for an entire one-minute segment, it would provide 480 ticks and deliver too much fluid for the selected flow rate. Consequently, the motor may be controlled such that it is active for only a portion of each time segment necessary to deliver 1 milliliter, and is inactive for the remainder of the time segment. In the present example, 1 milliliter is delivered in approximately 56 ticks, equivalent to about 7 seconds at a motor speed of 40 rpm.

During the remaining 53 seconds of the time segment, the motor is inactive. As may be understood, the therapy delivery rate may be adjusted without changing the motor speed (rpm) by changing the length of time the motor is active during each time segment.

As will be described in detail below, the present invention is embodied by a method wherein a fluid bolus is commanded and delivered at a higher flow rate if air-in-line exceeds a first threshold, and excess fluid delivered by the bolus is compensated for by temporarily reducing the flow rate relative to the selected therapy flow rate. In an embodiment of the present invention, the bolus may be 1.0 milliliters of fluid delivered at the priming flow rate of the pump, for example 700 ml/hr, which is higher than the maximum selectable flow rate for therapy. Of course, other bolus volumes and bolus flow rates may be used without straying from the invention.

Figure 3A:
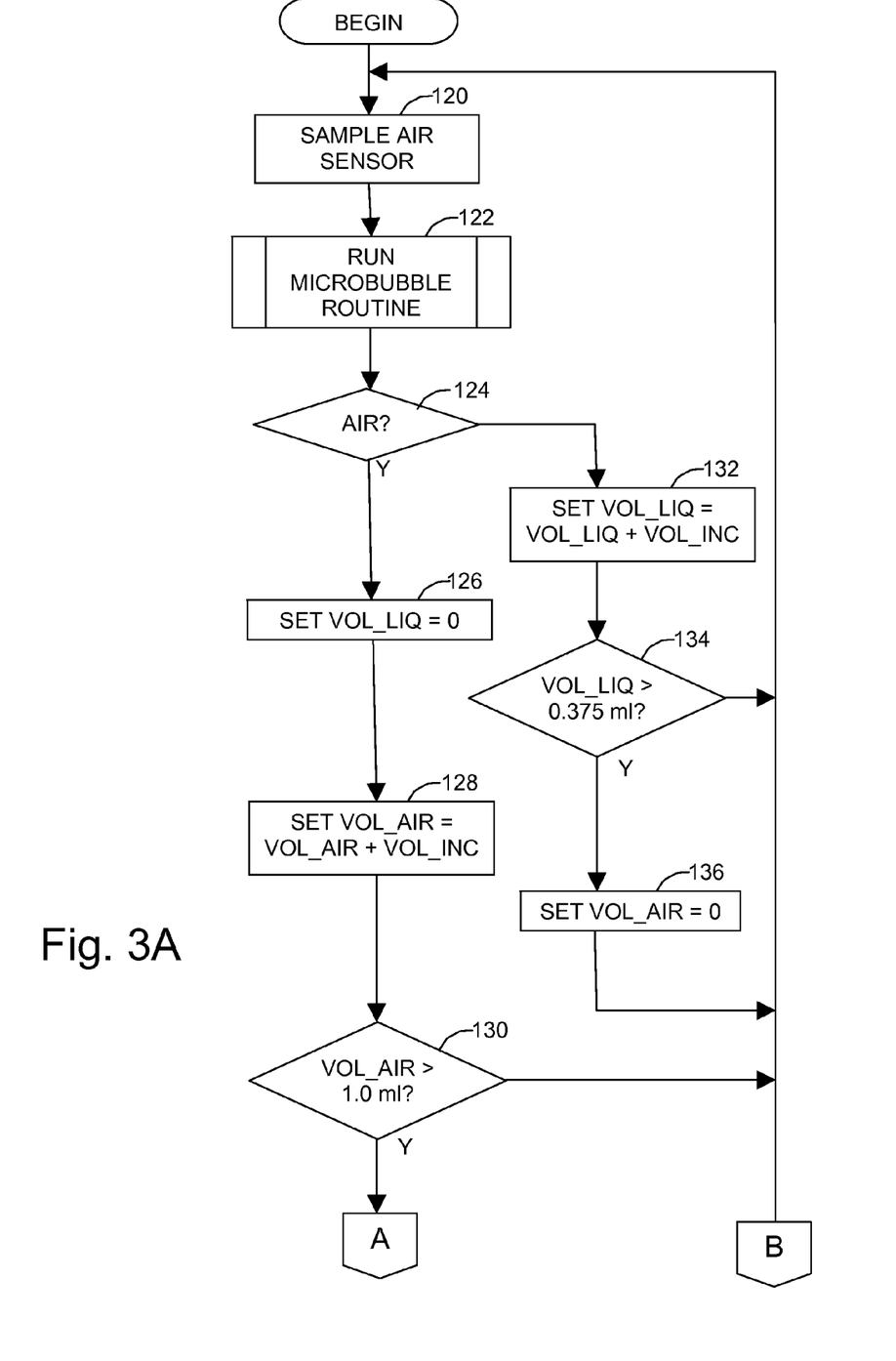
FIGS. 3A-3C are a flow diagram illustrating methodology for monitoring an air-in-line sensor of the infusion pump and detecting and air-in-line condition during therapy in accordance with an embodiment of the present invention.
Figure 3B:
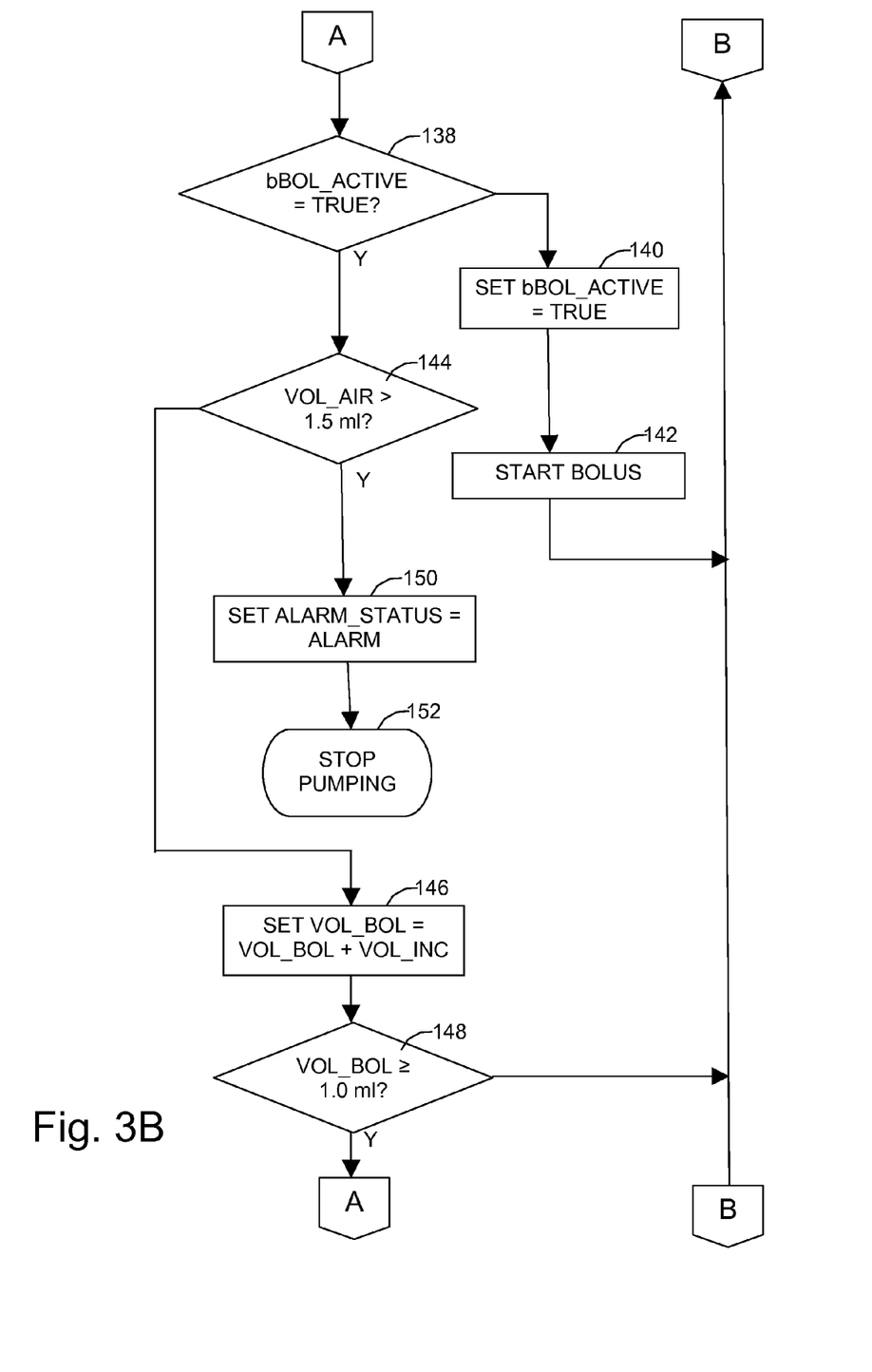
Figure 3C:
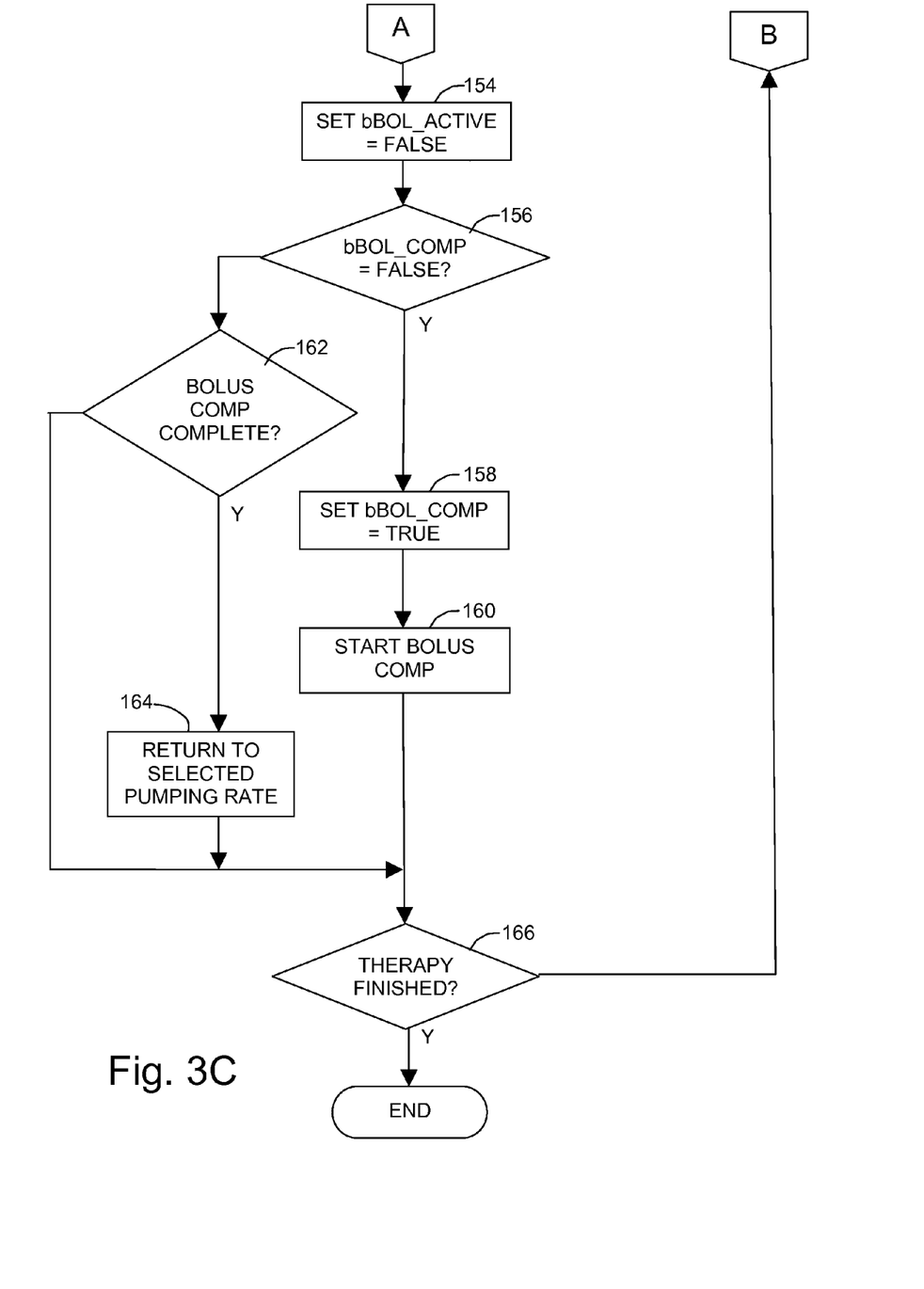

Attention is now directed to FIGS. 3A-3C, which generally illustrate air-in-line detection logic implemented by software routines stored and executed by the pump in accordance with an embodiment of the present invention. In the embodiment shown, the air-in-line sensor 26 is sampled in block 120. As described above, air-in-line sensor 26 provides a digital signal indicating that the sensor observed either air or liquid. In block 122, a microbubble routine is called which includes logic for disregarding very small foam bubbles. A form of the microbubble routine is described in detail below with reference to FIG. 4. If the incremental volume of fluid observed by sensor 26 is air, decision block 124 directs flow to blocks 126, 128, and 130. In block 126, a variable VOL_LIQ, which tracks the total volume of liquid observed since the sensor 26 last observed air, is set to zero. In block 128, a variable VOL_AIR, which tracks the total volume of air observed since the sensor 26 last observed a continuous threshold volume of liquid (e.g. 0.375 ml), is incremented by the addition of incremental volume VOL_INC, which corresponds to the volume moved past sensor 26 by one incremental step or "tick" of pump motor 20. By way of the example, in a current pump embodiment, the incremental volume is approximately 18 microliters. Thus, if the sampled sensor signal indicates air, in the present example, VOL_AIR is increased by 18 microliters. Decision block 130 checks whether VOL_AIR exceeds a first predetermined threshold, for example 1.0 milliliters. If not, flow loops back to handle the next sampled value from air-in-line sensor 26.

Returning to decision block 124, if the incremental volume of fluid observed by sensor 26 is liquid instead of air, then VOL_LIQ is incremented by VOL_INC in accordance with block 132. Decision block 134 determines if VOL_LIQ exceeds a predetermined threshold, which in the present embodiment is 0.375 ml. If so, VOL_AIR is set to zero in block 136 before flow loops back to handle the next sampled value from air-in-line sensor 26. If not, then decision block 134 bypasses block 136.

If decision block 130 determines that VOL_AIR exceeds the first threshold of 1.0 milliliters, then an inventive approach of the invention is used in an effort to avoid an air-in-line alarm condition if the accumulated air is due to microbubbles congregating at sensor 26. More particularly, when the total continuous volume of air exceeds the first threshold, the pump is commanded to deliver a bolus volume of fluid at a bolus flow rate greater than the therapy flow rate in an effort to clear the microbubbles away from the sensor. Decision block 138 in FIG. 3B checks the value of a Boolean variable bBOL_ACTIVE indicating whether a bolus is currently being delivered. If not, then flow moves to block 140 to set the value of bBOL_ACTIVE to True and then to block 142 to start the bolus delivery. Once the bolus is started, flow loops back to block 120.

If decision block 138 finds bBOL_ACTIVE to be True, it means bolus delivery was already commanded. In such a case, decision block 144 checks whether VOL_AIR exceeds a second predetermined threshold, for example 1.5 milliliters. If the second threshold is exceeded, then a delivered bolus failed to remove the air-in-line. Accordingly, an alarm condition is registered in block 150 and pumping is stopped in block 152. If VOL_AIR does not exceed the second threshold, then decision block 144 directs flow to block 146 to increment a variable VOL_BOL which tracks the bolus volume. In the present example embodiment, a bolus volume of 1.0 milliliters is used. Thus, decision block 148 loops flow back to block 120 until the fluid delivered in the bolus reaches 1.0 milliliters, at which point decision block 148 advances flow to block 154 in FIG. 3C. In block 154, the value of Boolean variable bBOL_ACTIVE is set to False now that bolus delivery is complete.

Next, the value of Boolean variable bBOL_COMP is checked in decision block 156. The value of bBOL_COMP indicates whether bolus compensation is underway. If the value of bBOL_COMP is False, then flow is directed to block 158 to set the value of bBOL_COMP to True and then to block 160 to start bolus compensation. Bolus compensation schemes embodying the present invention are described later with reference to FIGS. 5 and 6A-6D. If the value of bBOL_COMP is True at decision block 156, then flow branches to decision block 162 to check if bolus compensation is completed. If so, the pump is returned in block 164 to its originally selected pumping rate for the therapy.

Finally, a decision block 166 evaluates whether the programmed therapy is finished. If not, flow loops back to block 120 in FIG. 3A.

Figure 4:
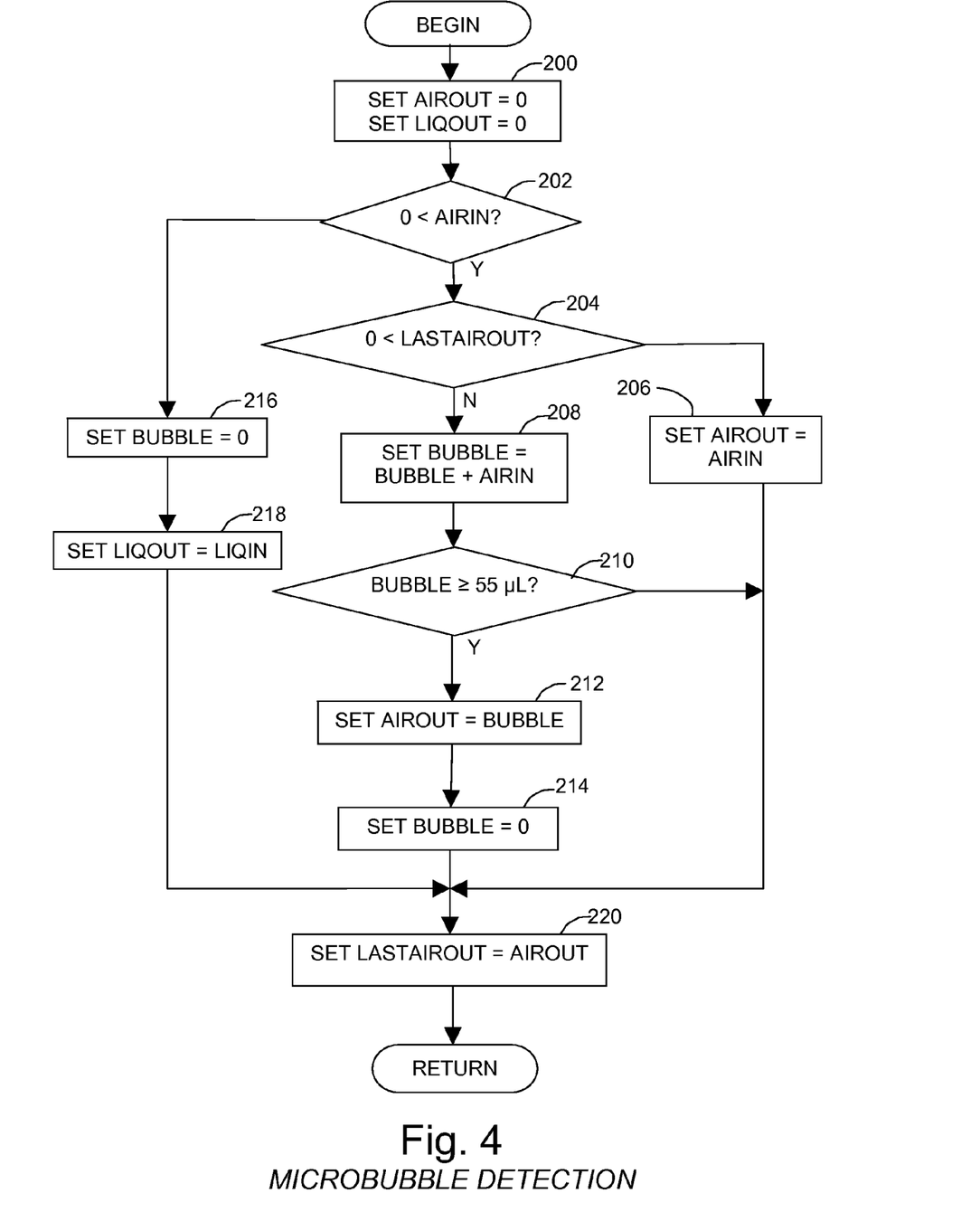
FIG. 4 is a flow diagram of a microbubble detection routine that determines if a volume of fluid observed by the air-in-line sensor is air or liquid in accordance with an embodiment of the present invention.

As mentioned above, a microbubble routine may be executed at block 122 to account for foam bubbles. Foam bubbles may form if the liquid source, such as a container of nutritional liquid, is vigorously shaken to mix the contents. A microbubble routine suitable for practicing the present invention is illustrated in FIG. 4. The routine may accept inputs AIRIN and LIQIN, which represent the volume of air and the volume of liquid, respectively, in the sampled incremental volume of fluid moved by the latest pump tick and observed by sensor 26. In the present example where each motor tick corresponds to about 18 microliters, AIRIN will have either a value of 18 microliters if air-in-line sensor 26 sees air or a value of zero if air-in-line sensor 26 sees liquid. Conversely, LIQIN will have a value that is either zero if air-in-line sensor 26 sees air or 18 microliters if air-in-line sensor 26 sees liquid.

The microbubble routine returns outputs AIROUT and LIQOUT. The routine is designed to look for consecutive occurrences of air until a predetermined threshold volume is reached before returning a non-zero value of AIROUT. In a current embodiment, the value of AIROUT is held at zero until AIRIN indicates air for four consecutive calls of the routine, at which point the sensor readings are deemed to indicate a real air bubble that may possibly trigger an air-in-line alarm, rather than merely indicating foam bubbles. At this point, the four readings are accumulated into a single AIROUT value (e.g. 72 microliters). Thus, the value of AIROUT will initially jump from zero to four times the volume resolution (e.g. 72 microliters) when a significant volume of air is detected. Once this threshold has been reached, AIROUT is set to AIRIN in subsequent calls of the routine until the chain of consecutive air readings is broken by a liquid reading. If successive values of AIRIN fluctuate between zero and a nonzero value (e.g. 18 microliters) without reaching four consecutive nonzero values, it is an indication that foam bubbles are present, and the AIRIN values will be disregarded. If the value of LIQIN is greater than zero, then the value of LIQOUT will be set equal to the value of LIQIN. As may be appreciated, the microbubble routine helps reduce false air-in-line alarms by disregarding small air bubbles indicative of foam.

An embodiment of the microbubble routine is shown in FIG. 4. An initial block 200 of the depicted microbubble routine sets the values of AIROUT and LIQOUT to zero. A decision block 202 checks the value of AIRIN. If the value of AIRIN is greater than zero (e.g. 18 microliters), sensor 26 sees air rather than liquid in the sampled volume increment, and flow proceeds to decision block 204. In decision block 204, the value of a variable LASTAIROUT is compared to zero. LASTAIROUT stores the value of AIROUT resulting from the previous call of the microbubble routine. So, decision block 204 determines whether the previous call of the routine found air. If air was seen in the previous call, then flow branches to block 206, wherein the value of AIROUT is set equal to the value of AIRIN. In other words, the routine keeps counting air if air was found previously.

If LASTAIROUT equals zero at decision block 204, then flow is directed to block 208 to set the value of a variable BUBBLE, which accumulates an air bubble volume over successive calls of the routine. Block 208 increments the value of BUBBLE by the value of AIRIN. Decision block 210 compares the value of BUBBLE to a predetermined threshold volume. In the present example, the threshold volume is 55 microliters, however another threshold volume may be chosen. As may be understood, four consecutive air readings of 18 microliters are required for the value of BUBBLE to surpass the threshold volume of 55 microliters. If the threshold is not reached, flow bypasses blocks 212 and 214, and the value of AIROUT remains at zero. If, however, decision block 210 finds the threshold has been reached, then block 212 sets the value of AIROUT equal to the value of BUBBLE, and block 214 resets the value of BUBBLE to zero.

Attention is returned now to decision block 202. If sensor 26 sees liquid instead of air, then AIRIN will equal zero and decision block 202 will direct flow to blocks 216 and 218. Block 216 resets the value of BUBBLE to zero, and block 218 sets the value of LIQOUT equal to the value of LIQIN.

Regardless of the logic flow path, flow will reach block 220 wherein the value of LASTAIROUT is set equal to AIROUT before the routine returns the values of AIROUT and LIQOUT to the calling program.

Figure 5:
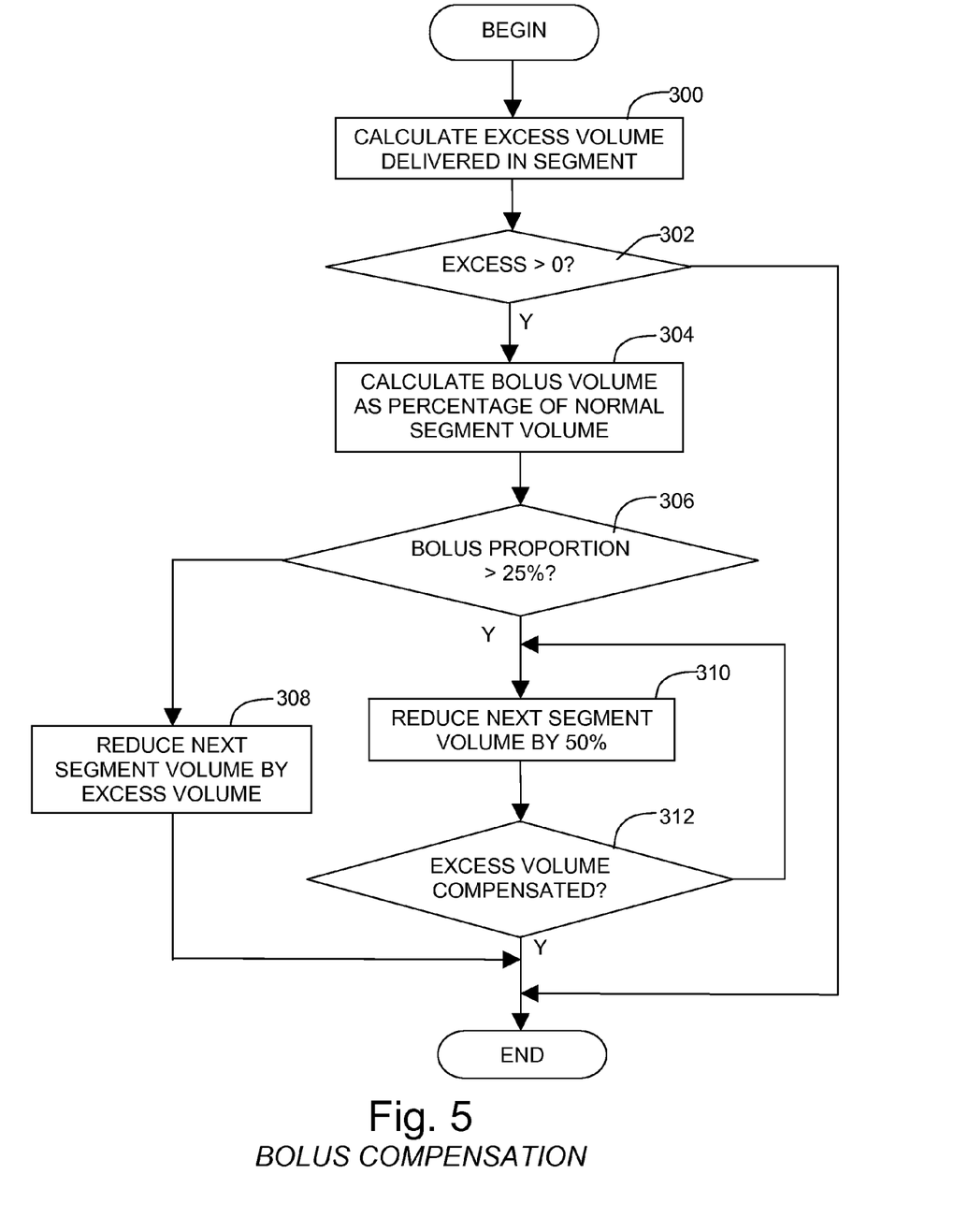
FIG. 5 is a flow diagram illustrating bolus compensation logic implemented by the pump in accordance with an embodiment of the present invention.

Description of bolus compensation according to an embodiment of the present invention will now be provided with reference to FIGS. 5 and 6A-6D. When a bolus is delivered by the pump in accordance with block 142 of FIG. 3B, subsequent pump control and operation must be modified to compensate for excess fluid delivered in the bolus "ahead of schedule." An exemplary embodiment of bolus compensation logic implemented by the pump is illustrated in FIG. 5. In block 300, a calculation of excess fluid volume delivered in the time segment in which the bolus was delivered is made. In some cases, the bolus can be delivered within the normal segment volume for the programmed therapy, such that the excess volume is zero. In these cases, there is no need for compensation. Thus, and initial decision block 302 checks whether the calculated excess volume is greater than zero, and if not, then bolus compensation is completely bypassed. If the excess volume calculation results in a volume greater than zero, then flow proceeds to block 304, wherein a calculation of the bolus volume as a percentage of the normal segment volume is performed. Decision block 306 then branches flow based on whether the bolus proportion calculated in block 304 is greater than a predetermined threshold percentage, for example 25%. If not, then flow branches to block 308 and the next segment volume is reduced by the excess volume calculated in block 300. In other words, the entire bolus compensation is achieved in the segment immediately following the bolus delivery segment. If decision block 306 determines that the bolus proportion is greater than the predetermined threshold percentage (e.g. 25%), then compensation for bolus overage will be spread over a plurality of subsequent segments by implementing a reduction rule. For example, the volume delivered in the next segment is reduced by 50% or some other factor as indicated in block 310. The reduction rule is implemented in successive segments until the excess volume is compensated for as confirmed by decision block 312.

Figure 6A:
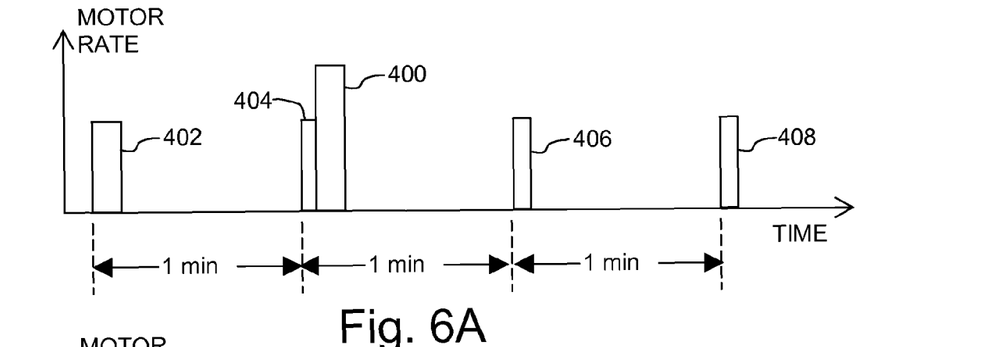
FIGS. 6A-6D are graphs showing motor rate versus time under various conditions wherein a bolus is delivered to remove microbubbles from the air-in-line sensor zone and subsequently compensated for in accordance with exemplary embodiments of the present invention.

FIGS. 6A-6D provide four examples of how the bolus compensation logic operates under actual pumping conditions. In FIG. 6A, it is assumed that the therapy flow rate of the pump is selected to be less than 60 milliliters per hour. Fluid delivery is scheduled in one-minute segments, wherein block 402 represents the period of motor activity during a normal segment of the therapy. In the next segment, delivery of a bolus occurs about half-way through the scheduled pumping period 404 as represented by block 400. As may be seen, the motor rate is increased during bolus delivery relative to the motor rate used during normal therapy delivery in order to achieve a high flow rate in excess of the maximum selectable therapy flow rate so that the bolus volume is delivered in a short period of time. The volume delivered by the bolus (e.g. 1.0 milliliter) is greater than 25% of the volume that would be delivered during the segment at the normal therapy flow rate (less than 1.0 milliliters assuming therapy flow rate is less than 60 milliliters per hour). Consequently, under the logic of FIG. 5, the volume pumped during subsequent segments is reduced by 50% relative to the normal segment volume until the excess volume delivered from the bolus is compensated for; this may be seen in blocks 406 and 408, which are not as wide as block 402, indicating that pump activity time is reduced for these segments. If an alarm is avoided, the segments will return to the selected therapy pumping rate (e.g. block 402) once compensation is complete.

Figure 6B:
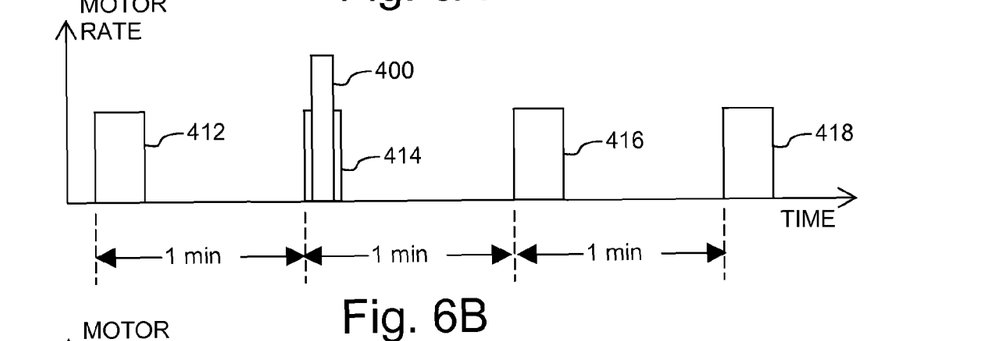

FIG. 6B illustrates a situation wherein the selected therapy flow rate is greater than 60 milliliters per hour and the bolus 400 is delivered relatively early within a segment. In this case, the entire bolus volume is delivered within the segment volume such that the total volume delivered during the segment is equal to the volume which was already scheduled (block 414) under the selected therapy flow rate. In this situation, no compensation is needed and the logic of FIG. 5 bypasses compensation. Consequently, blocks 412, 416, and 418 are identical and correspond to the therapy flow rate.

Figure 6C:
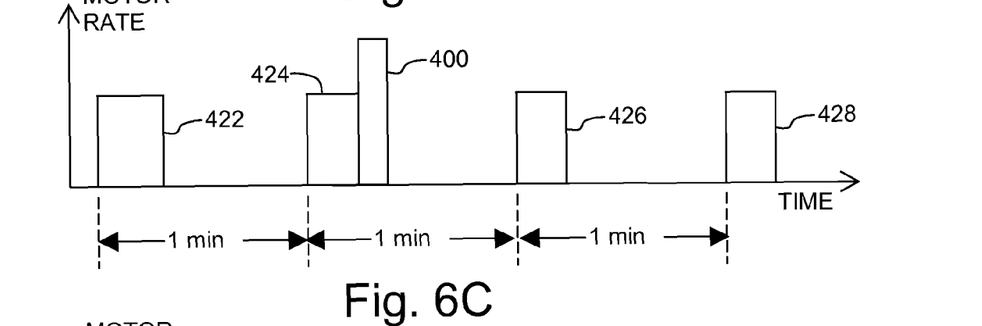

FIG. 6C represents a situation similar to that of FIG. 6A, however the therapy flow rate is greater than 150 milliliters per hour. The higher therapy rate can be understood by comparing block 422 to block 402 to observe that the motor is kept active for a longer period of time during the segment associated with block 422. The bolus 400 is delivered during scheduled block 424. Despite the higher flow rate, the bolus volume is still greater than 25% of the scheduled segment volume, and therefore subsequent segments are subject to the 50% volume reduction until compensation for excess volume is complete. The reduction can be seen in the shorter duration of blocks 426 and 428 relative to block 422. The time required to complete compensation decreases as therapy flow rate increases.

Figure 6D:
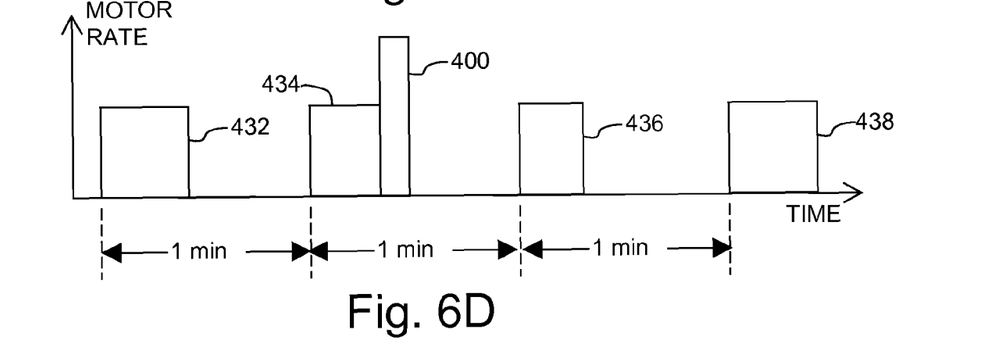

FIG. 6D illustrates a situation wherein the therapy flow rate exceeds 240 milliliters per hour. The motor is kept active for a longer period of time within each segment, as indicated by the width of block 432, to achieve the therapy flow rate. A bolus 400 is triggered near the end of the active pumping period 434. In this case, the bolus volume (e.g. 1.0 milliliter) is less than 25% of the segment volume delivered under the selected therapy rate (greater than 4.0 milliliters assuming therapy flow rate is greater than 240 milliliters per hour). Here, the logic of FIG. 5 will cause the next segment to be reduced by the entire bolus volume, as illustrated by block 436, such that compensation is achieved entirely within one segment. Block 438 corresponds to the scheduled segment volume in accordance with the therapy flow rate, and thus block 438 is identical to block 432.

The present invention is embodied as methods and a pump apparatus programmed to perform the methods. Example embodiments of the methods and pump apparatus of the present invention are described in detail herein, however those skilled in the art will realize that modifications may be made without straying from the spirit and scope of the invention as defined by the appended claims.

What is claimed is:

1. A method of detecting an air-in-line condition with respect to flow of liquid through tubing connected to an infusion pump, the method comprising:
providing an air-in-line sensor at a sensing location along the tubing, the air-in-line sensor generating a signal indicating whether a volume of fluid observed by the sensor at a given time is air or liquid;
operating the pump to deliver fluid at a therapy flow rate;
sampling the sensor signal as fluid flows past the sensor;
calculating a total volume of air observed by the sensor since the sensor last observed liquid;
operating the pump to deliver a bolus volume of fluid at a bolus flow rate greater than the therapy flow rate when the total volume of air exceeds a first threshold, wherein the bolus volume is delivered automatically by the pump, prior to stopping the pump or signaling an alarm, when the total volume of air exceeds the first threshold;
detecting the air-in-line condition when the total volume of air exceeds a second threshold greater than the first threshold, wherein the air-in-line condition is basis for stopping the pump or signaling the alarm.

2. The method according to claim 1, further comprising the step of operating the pump to deliver fluid at a reduced flow rate less than the therapy flow rate after delivery of the bolus volume.

3. The method according to claim 2, wherein the pump is operated to deliver fluid at the reduced flow rate until an excess volume delivered relative to the therapy flow rate as a result of the delivery of the bolus volume is compensated for.

4. The method according to claim 3, further comprising the step of operating the pump to deliver fluid at the therapy flow rate after the excess volume has been compensated for.

5. The method according to claim 3, wherein the pump is operated according to equal time segments, and the reduced flow rate is applied over a plurality of the time segments subsequent to the time segment in which the bolus volume is delivered.

6. The method according to claim 5, wherein the plurality of time segments are consecutive time segments.

7. The method according to claim 6, wherein the plurality of consecutive time segments immediately follow the time segment during which the bolus volume was delivered.

8. The method according to claims 3, wherein the pump is operated according to equal time segments, and the reduced flow rate is applied only to a single time segment subsequent to the time segment in which the bolus volume is delivered.

9. The method according to claim 8, wherein single time segment immediately follows the time segment during which the bolus volume was delivered.

10. A method of clearing air microbubbles from an observation zone of an air-in-line sensor arranged to observe fluid flowing through tubing connected to an infusion pump, wherein the pump is programmed to deliver fluid at a therapy flow rate, the method comprising:
calculating a total volume of air observed by the sensor since the sensor last observed liquid; and
operating the pump to deliver a bolus volume of fluid at a bolus flow rate greater than the therapy flow rate when the total volume of air exceeds a predetermined threshold;
wherein the bolus volume is delivered automatically by the pump prior to stopping the pump or signaling an alarm when the total volume of air exceeds the predetermined threshold.

11. The method according to claim 10, wherein the infusion pump has a predetermined priming flow rate at which the pump is operated for priming the pump, and the bolus flow rate is substantially equal to the priming flow rate.

12. An infusion pump comprising:
a pumping mechanism operable to cause fluid flow through tubing connected to the pumping mechanism, the pumping mechanism including a motor and a motor controller for energizing the motor;

an air-in-line sensor arranged at a sensing location along the tubing to observe fluid flowing through the tubing, the air-in-line sensor generating a signal indicating whether a volume of fluid observed by the sensor at a given time is air or liquid;

a memory module; and a microprocessor connected to the memory module, the pumping mechanism and the air-in-line sensor, wherein the microprocessor is programmable to command the pumping mechanism deliver fluid at a therapy flow rate;

wherein the memory module stores programming instructions causing the microprocessor to command the pumping mechanism to deliver a bolus volume of fluid at a bolus flow rate greater than the therapy flow rate in response to signals from the air-in-line sensor indicating an uninterrupted volume of air flowing through the tubing is greater than a predetermined first volume threshold, wherein the bolus volume is delivered automatically by the pump prior to stopping the pump or signaling an alarm;

wherein the memory module stores programming instructions causing the microprocessor to register an air-in-line alarm condition in response to signals from the air-in-line sensor indicating an uninterrupted volume of air flowing through the tubing is greater than a predetermined second volume threshold greater than the first volume threshold, wherein the microprocessor commands the pump to stop or signals the alarm upon registering the air-in-line alarm condition.

13. The infusion pump according to claim 12, wherein the memory module stores programming instructions causing the microprocessor to command the pumping mechanism to deliver fluid at a reduced flow rate less than the therapy flow rate after delivery of the bolus volume until an excess volume delivered relative to the therapy flow rate as a result of the delivery of the bolus volume is compensated for.

14. The infusion pump according to claim 13, wherein the reduced flow rate is a predetermined percentage of the therapy flow rate.

15. The infusion pump according to claim 14, wherein the predetermined percentage is 50%.

16. The infusion pump according to claim 13, wherein the memory module stores programming instructions causing the microprocessor to command the pumping mechanism to deliver fluid at the therapy flow rate after the excess volume has been compensated for.

* * * * *